United States Patent [19]

Bonse et al.

[11] 4,443,629

[45] Apr. 17, 1984

[54] PREPARATION OF HYDRAZIDINES

[75] Inventors: Gerhard Bonse, Cologne; Thomas Schmidt, Haan, both of Fed. Rep. of Germany

[73] Assignee: Bayer Aktiengesellschaft, Leverkusen, Fed. Rep. of Germany

[21] Appl. No.: 387,907

[22] Filed: Jun. 14, 1982

[30] Foreign Application Priority Data

Jul. 3, 1981 [DE] Fed. Rep. of Germany ....... 3126388

[51] Int. Cl.³ .......................................... C07C 123/02
[52] U.S. Cl. .................................................. 564/226
[58] Field of Search ................................ 564/250, 226

[56] References Cited

PUBLICATIONS

Journal of Heterocyclic Chemistry, vol. 12, No. 6, pp. 1143–1153.
Justus Liebigs Annalen der Chemie, vol. 749, 1971, pp. 16–23.
Justus Liebigs Annalen der Chemie, 1975, pp. 1120–1123.

*Primary Examiner*—Natalie Trousof
*Assistant Examiner*—L. Hendriksen

*Attorney, Agent, or Firm*—Sprung, Horn, Kramer & Woods

[57] ABSTRACT

A one-step process for the preparation of hydrazidines of the general formula

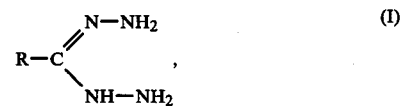

in which R represents an optionally substituted alkyl group, an optionally substituted cycloalkyl group, an optionally substituted aryl group or an optionally substituted aralkyl group, or their acid addition salts, in high yield, comprises reacting appropriate amidines or their acid addition salts with hydrazine in solvents at reduced pressure and at temperatures between −80° C. and +100° C., the reaction being effected in the presence of water present in the solvent and/or in the hydrazine by employing it as hydrazine hydrate. The hydrazidines of formula (I) and their salts are valuable intermediates in heterocyclic chemistry, for example for the synthesis of herbicidally active as-triazinones.

10 Claims, No Drawings

PREPARATION OF HYDRAZIDINES

The present invention relates to an unobvious process for the preparation of certain hydrazidines, most of which are known, starting from amidines.

It is already known that certain hydrazidines are obtained if, in a first step, the amidinium salt of a carboxylic acid is converted with hydrazine into an amidrazone salt; after the amidrazone salt has been isolated, the reaction mixture is reacted, in a second step, with anhydrous hydrazine in an anhydrous solvent and is then warmed at 40° C. under reduced pressure (approx. 480 mbar) for some time, and, after removing the solvent, the corresponding hydrazidine salt is obtained (see Liebigs Ann. Chem. 749, pages 16–23 (1971) and Liebigs Ann. Chem. 1975, pages 1,120–1,123).

Acethydrazidine hydrochloride can be obtained in this way, starting from acetamidine hydrochloride, in an overall yield of 83% of theory.

This two-step process has the disadvantage, however, that, in addition to intermediate isolation of the amidrazone, further reaction with anhydrous hydrazine in an anhydrous solvent is necessary. This implies substantial technical expense; and, furthermore, working with anhydrous hydrazine in the industrial synthesis represents a safety risk.

The present invention now provides a process for the production of a hydrazidine of the general formula

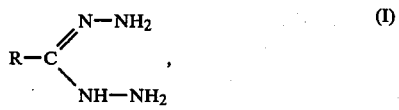

in which R represents an optionally substituted alkyl group, an optionally substituted cycloalkyl group, an optionally substituted aryl group or an optionally substituted aralkyl group, or an acid addition salt thereof, starting from a corresponding amidine, characterized in that an amidine of a carboxylic acid of the general formula

in which R has the meaning given above, or an acid addition salt thereof, is reacted with hydrazine hydrate ($NH_2-NH_2 \times H_2O$) in a technical solvent (containing water), under reduced pressure and at a temperature between about $-80°$ C. and $+100°$ C. It is surprising that compounds of formula (I) and their salts can be obtained in very good yields and in a very pure form by the novel one-step procedure of the present invention.

The process according to the invention exhibits a number of advantages. In addition to significantly higher yields, it is particularly advantageous to carry out the overall reaction as a "one-pot reaction". Furthermore, hydrazine hydrate and technical solvents, that is to say solvent containing water, can be used instead of anhydrous hydrazine and absolute solvents.

The preferred hydrazidines of formula (I), and their salts, which can be prepared by the process according to the present invention are those,
in which R represents an optionally substituted, straight-chain or branched alkyl group with 1 to 12 carbon atoms, an optionally substituted cycloalkyl group with 3 to 6 carbon atoms, an optionally substituted aryl group with 6 or 10 carbon atoms or an optionally substituted aralkyl group with 6 or 10 carbon atoms in the aryl part and 1 to 4 carbon atoms in the alkyl part.

Suitable substituents on the previously mentioned optionally substituted groups of radical R are any of those substituents which do not react with hydrazine hydrate under the reaction conditions.

For example, the alkyl radicals can be substituted by halogen (particularly chlorine or fluorine) or by alkoxy or alkylthio with 1 to 4 carbon atoms in each case.

The cycloalkyl radicals can, for example, be substituted by halogen (particularly chlorine or fluorine), by alkyl, alkoxy or alkylthio with 1 to 4 carbon atoms in each case, or by phenyl (which is itself optionally substituted).

The aryl and aralkyl radicals can be substituted, for example, by halogen (preferably fluorine, chlorine or bromine), by nitro, by alkyl, alkoxy or alkylthio with 1 to 4 carbon atoms in each case or by halogenoalkyl, halogenoalkoxy or halogenoalkylthio with 1 to 4 carbon atoms and up to 5 identical or different halogen atoms (particularly fluorine and chlorine atoms) in each case.

Particularly preferred compounds of formula (I) prepared by the process of the present invention are those in which R represents a methyl, chloromethyl, ethyl, n-propyl, isopropyl, n-butyl, sec.-butyl, tert.-butyl, cyclopropyl, cyclobutyl, cyclopentyl, cyclohexyl, phenyl or benzyl group.

If, for example, acetamidine hydrochloride and hydrazine hydrate are used as the starting materials, the course of the reaction according to the present invention is illustrated by the following equation:

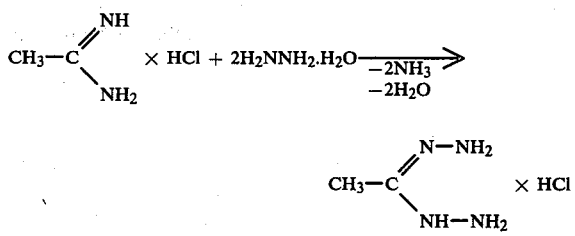

Preferred amidines of formula (II) required as starting materials for carrying out the process according to the invention are those in which R represents those radicals which have already been mentioned as substituents in connection with the description of the preferred and particularly preferred compounds of the formula (I).

The amidines of the formula (I) and their acid addition salts are compounds generally known in organic chemistry, and/or can be prepared by known processes (see Org. Synthesis Coll. Vol. I, page 5 (1951); Beilstein Vol. 2, page 185; Vol. 2/III, page 452; Vol. 2/III, page 478; and Vol. 9, page 280).

Examples which may be mentioned are: acetamidine, chloroacetamidine, trichloroacetamidine, propionamidine, butyramidine, isobutyramidine, valeramidine, benzamidine and their hydrochlorides; preferably acetamidine hydrochloride.

Suitable diluents for the reaction according to the invention are inert organic solvents, which can all be in the form of technical solvents containing up to about 20% of water, e.g. about 0.1 to 20%.

These include as preferences, alcohols (such as methanol, ethanol, n-propanol, isopropanol, n-butanol, isobutanol, tert.-butanol, glycol, glycerol, amyl alcohol, cyclohexanol, 2-methylpentan-4-ol, methylglycol, n-hexanol, isohexyl alcohol, isoheptyl alcohol, n-heptanol, nonyl alcohol, dedecyl alcohol or methylcyclohexanol), ethers (such as tetrahydrofuran, dioxane or ethylene glycol monomethyl ether), amides (such as dimethylformamide, diethylformamide, dimethylacetamide or N-methylpyrrolidone), hydrocarbons (such as benzene or toluene), and halogenated hydrocarbons (such as methylene chloride, chloroform, carbon tetrachloride, 1,2-dichloroethane, 1,1,2-trichloroethane, trichloroethylene and chlorobenzene). Appropriate mixtures of solvents can also be used.

The reaction is carried out under reduced pressure, in order to remove the ammonia liberated in the reaction from the reaction mixture. It is appropriate to work in the range of pressure from 0.1 to 800 mbar, preferably working at pressures between 50 and 300 mbar.

The reaction temperatures can vary within a relatively wide range, and depend on the pressure used in each case. The reaction can, as mentioned above, be carried out in the temperature range from $-80°$ C. to $+100°$ C.; it is preferably carried out between $-30°$ C. and $+50°$ C. The process can be carried out continuously or discontinuously.

For carrying out the process according to the invention, in general 2 to 2.5 mols, preferably 2 to 2.3 mols, of hydrazine hydrate are employed per mol of the amidine of the formula (II) or its corresponding acid addition salt.

The isolation of the products of the process, of the formula (I), is effected in the customary manner by removal of the solvent. The hydrazidines or acid addition salts of hydrazidines which are produced by the process according to the invention in high yield and in high purity can preferably be reacted as a solution or suspension to give secondary products, without isolation.

Hydrazidines are valuable structural units for the synthesis of numerous heterocyclic compounds, and here particularly for herbicidally active as-triazinones (see Liebigs Ann. Chem. 1976, pages 2,206–2,221; ibid. 1975, pages 1,120–1,123; Chem. Ber. 108, pages 3,509–3,517 (1975); Chem. Ber. 112, pages 1,981–1,990 (1979); German Published Specifications DOS Nos. 2,224,161 and 2,556,835 and U.S. application Ser. No. 338,811, filed Jan. 11, 1982 now pending).

The following example merely illustrates the process of the present invention in more detail.

PREPARATIVE EXAMPLE

Example 1

Acethydrazidine hydrochloride

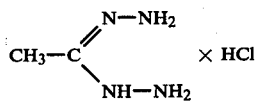

A suspension of 30 g (0.3 mol) of acetamidine hydrochloride (95% pure) in 200 ml of technical ethanol containing about 5% of water in a liter three-necked flask was cooled to 5° C. and the pressure was reduced to 130 mbar. 31.4 g (0.62 mol) of hydrazine hydrate were then added dropwise with vigorous stirring, and stirring was continued for a further two hours. Ethanol was then removed in vacuo and 37.1 g of acethydrazidine hydrochloride were obtained, after drying, as colorless crystals, melting point 154° C. with a purity of 99% (determined by polarography), which corresponded to a yield of 95% of theory.

The compounds of the formula

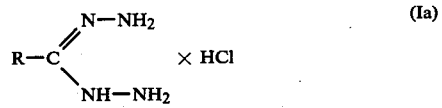

listed in the following table could also be prepared by the procedure described above in Example 1:

TABLE

| Compound No. | R | Yield (% of theory) | Melting point (°C.) |
| --- | --- | --- | --- |
| 2 | C$_2$H$_5$ | 85 | 109–112 |
| 3 | n-C$_3$H$_7$ | 81 | 105–115 |
| 4 | iso-C$_3$H$_7$ | 69 | 126–128 |
| 5 | ClCH$_2$ | 75 | 135–138 |
| 6 | Cl$_3$C | 60 | 112–115 |

It will be appreciated that the instant specification and examples are set forth by way of illustration and not limitation, and that various modifications and changes may be made without departing from the spirit and scope of the present invention.

We claim:

1. In the production of a hydrazidine of the formula

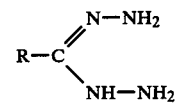

in which R is an optionally substituted alkyl group, an optionally substituted cycloalkyl group, an optionally substituted aryl group or an optionally substituted aralkyl group, or an acid addition salt thereof, by reacting the corresponding amidine of the formula

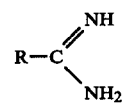

or an acid addition salt thereof with hydrazine, the improvement which comprises effecting the reaction with hydrazine hydrate in the presence of an organic solvent which may contain water under reduced pressure and at a temperature between about $-80°$ and $+100°$ C.

2. A process according to claim 1, wherein the solvent contains about 0.1 to 20% water.

3. A process according to claim 1, wherein the pressure ranges from about 0.1 to 800 mbar.

4. A process according to claim 1, wherein the temperature is between about $-30°$ and $+50°$ C.

5. A process according to claim 1, wherein about 2 to 2.5 mols of hydrazine hydrate are employed per mol of the amidine or acid addition salt thereof.

6. A process according to claim 1, in which R is an optionally substituted alkyl group with 1 to 12 carbon atoms, an optionally substituted cycloalkyl group with 3 to 6 carbon atoms, an optionally substituted aryl group with 6 or 10 carbon atoms or an optionally substituted aralkyl group with 6 or 10 carbon atoms in the aryl part and 1 to 4 carbon atoms in the alkyl part.

7. A process according to claim 1, in which R is a methyl, chloromethyl, ethyl, n-propyl, isopropyl, n-butyl, sec.-butyl, tert-butyl, cyclopropyl, cyclobutyl, cyclopentyl, cyclohexyl, phenyl or benzyl group.

8. A process according to claim 1, wherein the amidine is selected from the group consisting of acetamidine, chloroacetamidine, trichloroacetamidine, propionamidine, butyramidine, isobutyramidine, valeramidine, benzamidine and the hydrochlorides thereof.

9. A process according to claim 1, wherein the reactants are acetamidine hydrochloride and hydrazine hydrate.

10. A process according to claim 9, about 2 to 2.3 mols of hydrazine hydrate being employed per mol of amidine, the solvent containing about 0.1 to 20% of water, the temperature ranging from about $-30°$ to $+50°$ C. and the pressure ranging from about 50 to 300 mbar.

* * * * *